United States Patent
Watson

(10) Patent No.: US 12,151,032 B2
(45) Date of Patent: Nov. 26, 2024

(54) DECORATIVE SPLINT OR CAST MATERIAL

(71) Applicant: Bella Bling, LLC, Chelmsford, MA (US)

(72) Inventor: Cristina Watson, Chelmsford, MA (US)

(73) Assignee: Bella Bling, LLC, Chelmsford, MA (US)

( * ) Notice: Subject to any disclaimer, the term of this patent is extended or adjusted under 35 U.S.C. 154(b) by 1091 days.

(21) Appl. No.: 16/997,921

(22) Filed: Aug. 19, 2020

(65) Prior Publication Data

US 2021/0060202 A1 Mar. 4, 2021

Related U.S. Application Data

(63) Continuation of application No. 15/560,832, filed as application No. PCT/US2016/023942 on Mar. 24, 2016, now Pat. No. 10,765,773.

(Continued)

(51) Int. Cl.
*A61L 15/14* (2006.01)
*A61F 5/058* (2006.01)
(Continued)

(52) U.S. Cl.
CPC .............. *A61L 15/14* (2013.01); *A61F 5/058* (2013.01); *A61F 13/00991* (2013.01);
(Continued)

(58) Field of Classification Search
CPC ................ A61F 13/04; A61F 13/00991; A61F 5/05866; A61F 5/058; A61F 2013/00153;
(Continued)

(56) References Cited

U.S. PATENT DOCUMENTS 2,837,088 A * 6/1958 Moses ................... A61F 13/046
602/14
3,692,023 A 9/1972 Phillips et al.
(Continued)

FOREIGN PATENT DOCUMENTS

DE 42 18 498 A1 12/1993
EP 0 358 451 A1 3/1990
(Continued)

OTHER PUBLICATIONS

International Search Report and Written Opinion for International Application No. PCT/US2012/023580, mailed May 11, 2012.
(Continued)

*Primary Examiner* — Ophelia A Hawthorne
(74) *Attorney, Agent, or Firm* — Wolf, Greenfield & Sacks, P.C.

(57) ABSTRACT

A decorative splint material includes a moisture-curable material adapted to be wetted and molded into a splint configuration that conforms to an anatomical body part. The material hardens via a curing process to retain the splint configuration. The splint material includes a plurality of decorative elements integrated with the splint material. The decorative elements are provided on a substrate which is overlaid onto the moisture-curable material, and the substrate is overlaid with a flexible sheet having a plurality of openings which align with the decorative elements. The decorative elements are retained by the sheet of splint material when the sheet is wetted, molded into a splint configuration, and hardened.

9 Claims, 6 Drawing Sheets

Related U.S. Application Data

(60) Provisional application No. 62/137,607, filed on Mar. 24, 2015.

(51) Int. Cl.
    *A61F 13/00* (2024.01)
    *A61F 13/04* (2006.01)
    *A61L 15/07* (2006.01)
    *A61L 15/12* (2006.01)

(52) U.S. Cl.
    CPC .............. *A61F 13/04* (2013.01); *A61L 15/07* (2013.01); *A61L 15/12* (2013.01); *A61F 5/05866* (2013.01)

(58) Field of Classification Search
    CPC ........ A61F 13/041; A61L 15/14; A61L 15/12; A61L 15/07; Y10S 264/30
    See application file for complete search history.

(56) References Cited

U.S. PATENT DOCUMENTS

| | | | |
|---|---|---|---|
| 4,240,415 A | 12/1980 | Wartman | |
| RE30,541 E | 3/1981 | Larson | |
| 4,323,611 A | 4/1982 | Poll | |
| 4,661,535 A | 4/1987 | Borroff et al. | |
| 4,831,665 A * | 5/1989 | Palmaer | A61F 9/02 2/9 |
| 5,342,291 A | 8/1994 | Scholz et al. | |
| 5,439,438 A | 8/1995 | Ersfeld et al. | |
| 5,573,501 A | 11/1996 | Ruscito et al. | |
| 5,603,691 A | 2/1997 | Scholz et al. | |
| 5,913,840 A | 6/1999 | Allenberg et al. | |
| 6,074,354 A | 6/2000 | Scholz et al. | |
| 6,093,161 A | 7/2000 | Vlaeyen et al. | |
| 6,110,134 A | 8/2000 | Clark, Jr. et al. | |
| 6,673,029 B1 * | 1/2004 | Watson | A61F 13/04 602/6 |
| 7,089,764 B2 | 8/2006 | Brett | |
| 7,468,047 B2 | 12/2008 | Nieberding | |
| 8,545,422 B2 | 10/2013 | Watson | |
| 10,765,773 B2 | 9/2020 | Watson | |
| 2002/0069671 A1 | 6/2002 | Richardson | |
| 2005/0101899 A1 | 5/2005 | Wegmann | |
| 2006/0004313 A1 * | 1/2006 | Heinz | A61F 5/01 602/8 |
| 2007/0004993 A1 | 1/2007 | Coppens et al. | |
| 2007/0232979 A1 | 10/2007 | Montgomery | |
| 2007/0283597 A1 | 12/2007 | Logan | |
| 2009/0107615 A1 | 4/2009 | Wood | |
| 2010/0036300 A1 * | 2/2010 | Sheehan | A61F 5/05825 602/7 |
| 2010/0292620 A1 | 11/2010 | Lattimore | |
| 2012/0203155 A1 | 8/2012 | Watson | |
| 2018/0110894 A1 | 4/2018 | Watson | |

FOREIGN PATENT DOCUMENTS

| | | |
|---|---|---|
| EP | 2 233 812 A1 | 9/2010 |
| RU | 2 127 569 C1 | 3/1999 |
| RU | 79 759 U1 | 1/2009 |
| UA | 56 953 U | 1/2011 |
| WO | WO 97/04936 A1 | 2/1997 |
| WO | WO 2007/141789 A2 | 12/2007 |

OTHER PUBLICATIONS

International Search Report and Written Opinion for International Application No. PCT/US2016/023942, mailed Jun. 10, 2016.
International Preliminary Report on Patentability for International Application No. PCT/US2016/023942, mailed Oct. 5, 2017.
[No Author Listed] Cast Decorating Ideas Casttoo Tattoo. Supplies Central. Http://suppliescentral.blogspot.com/2009/03/cast-decorating-ideas-casttoo-castoo.html, 4 pages [accessed Aug. 2010].
[No Author Listed] Exciting Way to Decorate Your Leg or Arm Cast. OrthoTape. http://orthotape.com/casttoo_cast_tattoo.asp, 2 pages [accessed Aug. 2010].
[No Author Listed] Fabian Seibert. Suelz Kotlett. http://www.suelzkotlett.com/index.php?page=04, 1 page [accessed Aug. 2010].
[No Author Listed] What is Shrinkins? SHRINKins. http://shrinkins.com/index.html, 4 pages [accessed Aug. 2010].
PCT/US2012/023580, May 11, 2012, International Search Report and Written Opinion.
PCT/US2016/023942, Jun. 10, 2016, International Search Report and Written Opinion.
PCT/US2016/023942, Oct. 5, 2017, International Preliminary Report on Patentability.

* cited by examiner

DECORATIVE SPLINT OR CAST MATERIAL

RELATED APPLICATIONS

This Application is a continuation of U.S. application Ser. No. 15/560,832 filed Sep. 22, 2017, entitled "DECORATIVE SPLINT OR CAST MATERIAL" which is a National Stage filing under 35 U.S.C. § 371 of International Application PCT/US2016/023942, filed Mar. 24, 2016, which claims the benefit under 35 U.S.C. § 119(e) to U.S. Provisional Application Ser. No. 62/137,607, entitled "DECORATIVE SPLINT OR CAST MATERIAL" filed on Mar. 24, 2015, each of which is incorporated herein by reference in its entirety.

FIELD

Disclosed embodiments relate generally to splints and casts, and more specifically to materials used to make decorative splints and casts, and methods of manufacturing the materials.

BACKGROUND

Casts and splints are applied to patients to stabilize, immobilize and/or provide support to injured body parts. The casts or splints may be formed of a fiberglass material that is impregnated with a polyurethane resin. Typically, the flexible material is placed in water and a medical professional then molds the sheet to the portion of the patient being treated to form the splint or cast. As the material dries, it hardens to form the splint or cast.

SUMMARY

According to one embodiment, a method of manufacturing a decorative splint material includes providing layers of fiberglass fabric impregnated with a moisture-curable polyurethane resin. A substrate holding a plurality of discrete, three-dimensional decorative elements is overlaid onto the layers of fiberglass fabric, and a flexible sheet having a plurality of openings is overlaid onto the substrate. The openings align with the decorative elements such that at least a portion of the decorative elements are exposed through the openings.

According to a another embodiment, a method of applying a splint to a patient includes wetting a sheet of splint material, the splint material being integrated with a plurality of discrete, three-dimensional decorative elements, molding the sheet of splint material over an anatomical body part into a splint configuration, and allowing the sheet of splint material to cure until the splint material hardens to retain the splint configuration. The decorative elements remain integrated with the splint material during each act.

According to a further embodiment, a decorative splint material comprises a splint material, which when wetted and applied to an anatomical body part in a splint configuration, cures to retain the splint configuration. The decorative splint material further comprises a plurality of separate decorative elements integrated with the splint material, and the decorative elements are retained by the splint material when the splint material is wetted, molded into the splint configuration and allowed to harden into the splint configuration.

BRIEF DESCRIPTION OF THE FIGURES

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
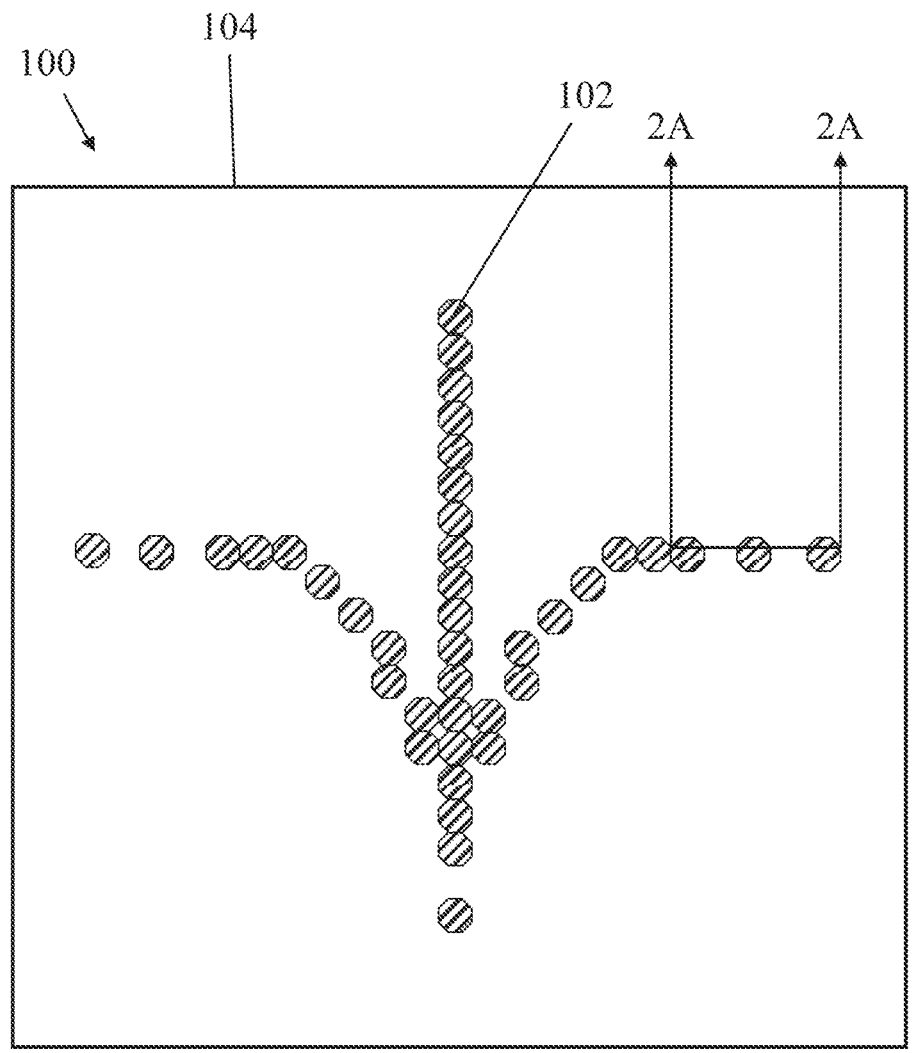
FIG. 1 is a top view of a sheet of splint or cast material including decorative elements according to one embodiment.

For ease of understanding, and without limiting the scope of the present disclosure, the devices to which this patent is addressed are disclosed below particularly in connection with splint materials and splints. For purposes herein, the term "splint material" means materials configured to be used in a splint, a cast, or other apparatus configured to support, stabilize, and/or immobilize an anatomical body part. Similarly, for purposes herein, the term "splint" means a splint, a cast, or other apparatus configured to support, stabilize, and/or immobilize an anatomical body part.

Splints are typically used when a person has been injured, has had surgery, or requires support, immobilization or stabilization for other medical reasons. Often, a patient may view the splint as unattractive and/or as a visual reminder of his or her injury. In some cases, these concerns may lead a patient to have a negative attitude regarding the splint, resist use of the splint, or perhaps request removal of the splint earlier than medically advisable.

Embodiments disclosed herein provide a visually appealing splint material which may aid in persuading a patient to properly use the splint, and also may improve a patient's outlook regarding their medical condition. Additionally, by providing a variety of decorative splint material options, a patient may be provided with a choice as to the visual appearance of his or her splint, which may allow a patient to express their particular style or color preference, thereby giving their splint a personalized or customized look.

According to some embodiments, a moisture-curable splint material includes decorative elements, such as rhinestones or plastic beads, which are integrated with the splint or cast material prior to applying the splint to the patient. When the splint material is wetted and wrapped shaped over a patient's body part, the decorative elements remain integrated with the material. Once the material hardens, a visually attractive splint is formed.

In some embodiments, the decorative elements (such as rhinestones, plastic beads, or other decorative elements) are integrated within the moisture-curable splint material during manufacturing of the splint material.

By providing a moisture-curable splint material with previously-integrated decorative elements, a patient may have a decorated splint applied without requiring a subsequent step of adding decorative elements to the splint. In particular, some embodiments allow a roll of material to be used to form a splint by wrapping a body part with an extended length of decorated material.

A moisture-curable fabric may be used to form a splint material. Moisture-curable fabrics may be flexible before exposure to moisture (e.g. water). After exposure to moisture, the fabric may remain flexible for an amount of time sufficient to mold the fabric into a desired shape, and may subsequently harden via a curing process such that the fabric maintains the desired shape.

One example of a moisture-curable fabric which may be used as a splint material is a knitted fiberglass fabric impregnated with a water-activated polyurethane resin, which has a curing time of approximately three minutes after being exposed to water. According to some embodiments, a moisture-curable fabric having a curing time between 2 minutes and 5 minutes, or any suitable curing time, may be used. In some embodiments, the curing time of a moisture-curable fabric may depend on various factors including, but not limited to, the temperature of the water, the rate at which the fabric is exposed to moisture, and the degree to which excess moisture is removed after the initial exposure.

The splint materials to which embodiments disclosed herein apply may be applied to a patient's arm, wrist, ankle, leg, nose or any other body part in need of support, stabilization and/or immobilization. In some embodiments, a moisture-curable splint material may be formed as a tape or sheet which may be wrapped around the anatomical body part to be treated. In some embodiments, a moisture-curable splint material may adhere to unprotected skin and/or clothing; in such embodiments, a protective underlayer may be applied to the body part before applying the moisture-curable splint material.

In other embodiments, a splint assembly including a moisture-curable splint material and one or more adhesive and/or padding layers may be adhered to a particular body part to be treated. In such embodiments, a splint assembly may be trimmed by a medical professional to a suitable size and shape according to the size and shape of the body part to be treated. In some embodiments, a splint assembly may be pre-cut or otherwise pre-shaped for a particular body part before being provided to the medical professional. In still further embodiments, a pre-cut or otherwise pre-shaped splint assembly may be provided, and the medical professional may perform additional trimming to customize the splint assembly before applying and curing.

A moisture-curable splint material may include decorative elements arranged in a specific design, such as shown in FIG. 1. In one illustrative embodiment shown in FIG. 1, a plurality of rhinestones 102 are included on a sheet 100 comprising at least one layer 104 of moisture-curable material, such a knitted fiberglass impregnated with a polyurethane resin. As shown in FIG. 1, some rhinestones 102 may be positioned directly adjacent to one or more rhinestones, while other rhinestones may be separated from their nearest neighbor rhinestones.

Figure 2A:
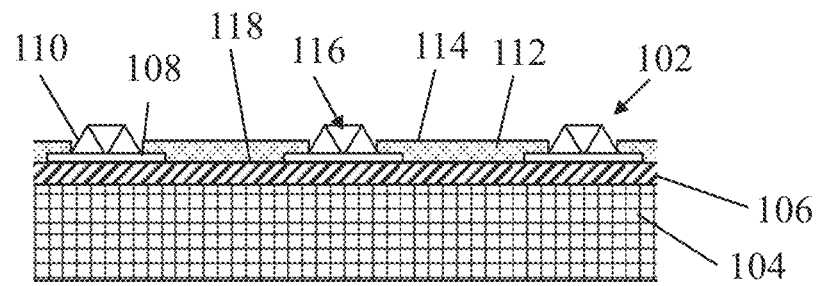
FIG. 2A is a partial cross-sectional view taken along line 2A-2A of FIG. 1.

FIG. 2A depicts a cross-sectional view of the embodiment of FIG. 1, taken along line 2A-2A. As shown in FIG. 2A, the rhinestones 102 are disposed on a substrate 106 which is placed over the layer 104 of moisture-curable material. The rhinestones include a base 108 which may be attached to the substrate 106, and a decorative upper portion 110. A flexible sheet 108 having a plurality of openings 116 overlays the substrate; the openings 116 are aligned with the rhinestones 102 such that at least a portion of the rhinestones are exposed.

In some embodiments, the base 108 of a rhinestone 102 may extend laterally beyond the decorative upper portion 110 such that the base is configured as a flange. The openings 116 in the flexible sheet 112 may be sized and positioned such that at least a portion of the flexible sheet overlaps a portion of the base 110. In such embodiments, the flexible sheet 112 may help to secure the rhinestones 102 to the substrate 106 and/or the layer 104 of moisture-curable material.

Figure 2B:
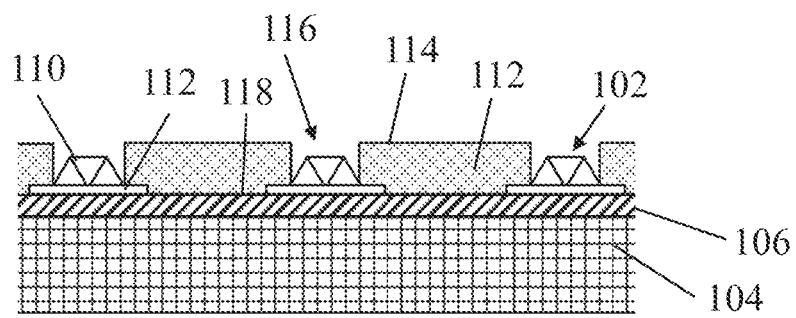
FIG. 2B is cross-sectional view of a splint or cast material including decorative elements according to another embodiment.

Although the embodiment depicted in FIG. 2A shows the rhinestones 102 as extending beyond an outer surface 114 of the flexible sheet 112, in some embodiments, the outer surface of the flexible sheet may be flush with, or may extend beyond the rhinestones. For example, FIG. 2B depicts one embodiment in which the outer surface 114 of the flexible sheet 112 extends beyond the rhinestones 102. In such embodiments, the openings 116 in the flexible sheet may be configured to at least partially expose the rhinestones.

In some embodiments, the flexible sheet 112 may be made from the same moisture-curable material as the layer 104. For example, the flexible sheet may comprise one or more layers of a knitted fiberglass fabric impregnated with a water-activated polyurethane resin. Of course the flexible sheet may alternatively comprise a different material than the layer 104. For example, in one embodiment, the flexible sheet may be made from an adhesive fabric such as a surgical tape. In such an embodiment, the adhesive may adhere to the substrate 106 and/or the layer 104 and may help to secure the rhinestones 102 within the sheet 100. Further, it should be understood that in some embodiments, additional layers of the moisture-curable material may be overlaid on the flexible sheet 112, as the disclosure is not so limited.

The flexible layer 112 (and any layers which may overlay the flexible layer) may have any suitable pattern of openings 116 such that the rhinestones 102 are at least partially exposed. In one embodiment, the flexible layer may include a plurality of openings which are aligned with each of the rhinestones; therefore the openings may feature substantially the same pattern and/or design as the rhinestones. In another embodiment, the openings 116 may be arranged as a grid, and the rhinestones may be patterned on a similar grid such that at least a portion of the rhinestones are aligned with a portion of the openings. In some embodiments, the flexible layer 112 may further include an adhesive bottom layer 118 which may at least partially secure the rhinestones 102 and/or the substrate 106 to the fiberglass layers 104.

Figure 2C:
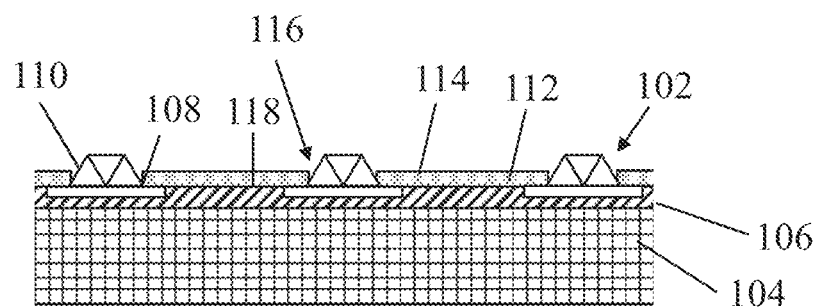
FIG. 2C is cross-sectional view of a splint or cast material including decorative elements according to yet another embodiment.

Depending on the particular embodiment, rhinestones 102 may be provided on any suitable substrate 106. For example, a substrate may comprise a flexible sheet such as a wire mesh, a mesh of plastic filaments, a flexible plastic sheet, or any other suitable flexible sheet to which rhinestones, or other decorative elements may be attached. Discrete rhinestones may be individually attached to a substrate using a suitable adhesive to create a desired pattern and/or design. Alternatively, a substrate having a plurality of rhinestones pre-attached also may be used. In some embodiments, rhinestones may be partially embedded in a substrate material, as shown in FIG. 2C. For example, a substrate 106 may comprise areas with a flexible thermoplastic material which may be heated to soften and/or partially melt the areas such that individual rhinestones 102 may be pressed into the thermoplastic material. Upon cooling, the thermoplastic material may retain the deformed shape and hold the rhinestones in place. In further embodiments, a substrate may not be included, and rhinestones 102 may be attached directly to a layer 104 of moisture-curable material, and subsequently overlaid by a flexible sheet, as described above.

Although the embodiments shown in FIGS. 1, 2A, 2B, and 2C have been described as including rhinestones, other types of decorative elements may be used, including beads (such as plastic, translucent beads), gemstones, crystals, jewels, or any other desired decorative elements as would be apparent to one of skill in the art. In some embodiments, combinations of different types of decorative elements may be used in the same material.

In embodiments where a large number of decorative elements are integrated with the splint material, the decorative elements may be positioned to provide bands free of decorative elements to facilitate trimming of the material. For example, in some embodiments, patterns of decorative elements may be provided wherein areas alternate between bands including decorative elements and bands not including decorative elements.

As shown in FIG. 1, the material may be in the form of a sheet having a square shape. However, sheets of other suitable shapes or configurations may be used with embodiments disclosed herein. For example, the sheet 100 shown in FIG. 1 may be a portion of an extended rectangular tape, and the tape may have a repeating or non-repeating pattern of decorative elements. In some embodiments, a tape may be provided in a roll. Alternatively, a trapezoidal shaped sheet (see FIG. 6a), a rectangular shaped sheet, a substantially triangular shaped sheet, a sheet having one or more curved edges (see FIG. 6b), or any other suitable sheet shape may be used. In some embodiments, sheets may be pre-cut into shapes which are intended for specific body parts, such as the nose, wrist or ankle.

In some embodiments, perforations may be included in a moisture-curable splint for breathability of the splint once in place on the patient. The perforations also may facilitate molding of the sheet when shaping the sheet into a splint on the patient. In some embodiments, decorative elements such as rhinestones may be positioned over one or more perforations. In other embodiments, decorative elements may be positioned off-center from perforations, or may be irregularly or randomly positioned relative to perforations. Of course, in some embodiments, a sheet of splint material may be provided without perforations, or the perforations may be provided only in certain sections of the sheet.

It is to be understood that the sheet of splint material need not necessarily be provided in a planar shape. For example, in some embodiments, a curved or bent piece of material may be provided and still be considered to be a sheet. With materials which are particularly flexible when not cured, a sheet of material may be provided as a roll of material.

Figure 3:
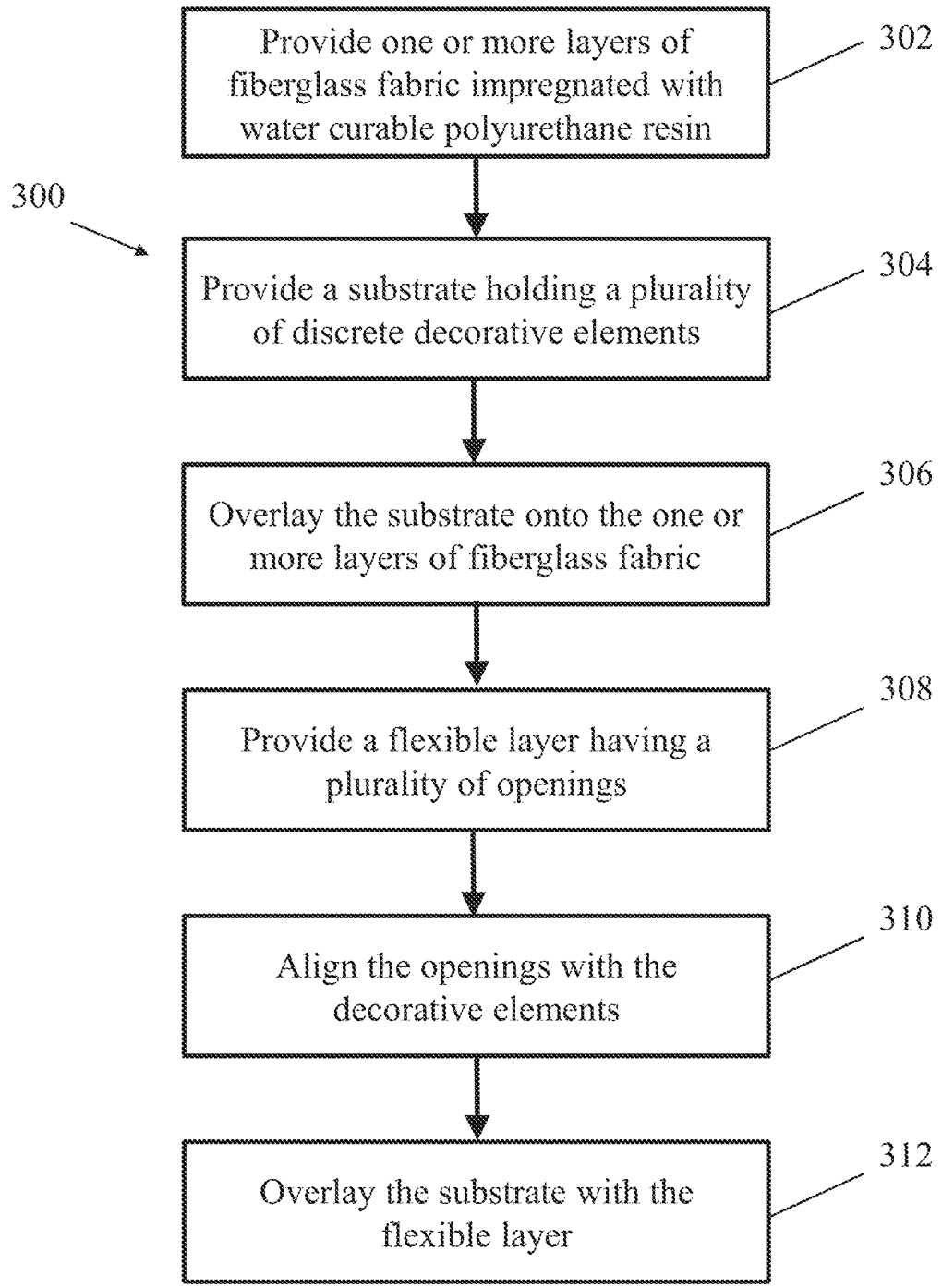
FIG. 3 is a flow chart of a method manufacturing a sheet of splint or cast material according to one embodiment.

Decorative elements may be integrated in the splint material during the process of forming the splint material. In one illustrative embodiment shown in FIG. 3, a method 300 of manufacturing a splint material includes incorporating decorative elements into a layered structure. The method includes providing one or more layers of fiberglass fabric impregnated with a moisture-curable polyurethane resin such as a water-curable polyurethane resin (act 302). In some embodiments, layers of fiberglass fabric may have been previously fabricated, and providing the layers may include simply acquiring the layers. A substrate holding a plurality of decorative elements is provided (act 304). The decorative elements may be arranged on the substrate in any suitable pattern and/or design, and may be attached to the substrate or may be simply placed on the substrate. The substrate holding the decorative elements is overlaid onto the one or more layers of fiberglass fabric (act 306). A flexible layer having a plurality of openings is provided (act 308) and the openings are aligned with the decorative elements (act 310). The flexible layer is overlaid onto the substrate (act 312) to secure the substrate and/or the decorative elements to the fiberglass layers.

As described above, in some embodiments, a flexible sheet may have more openings than the number of decorative elements. Therefore, in such embodiments, not all of the openings may be aligned with a decorative element, and the act 310 of aligning the openings with the decorative elements may involve aligning only a subset of the openings with the decorative elements.

In some embodiments, the decorative elements may be embedded into a substrate including areas of thermoplastic material by positioning the decorative elements on the substrate and pressing a block of planar material against the decorative elements. In other embodiments, the decorative elements may be pressed into the substrate by holding the decorative elements in a desired pattern on a plate and pressing heated areas of thermoplastic material against the decorative elements. The plate may be a flat plate with depressions or other components for holding the decorative elements in certain positions. The plate may be configured to hold decorative elements in a single pattern such that a single type of sheet of decorative elements may be repeatedly formed. Alternatively, the plate may have a grid pattern or other pattern of depressions to permit various designs to be formed by placing decorative elements in a selected subset of the depressions.

Figure 4:
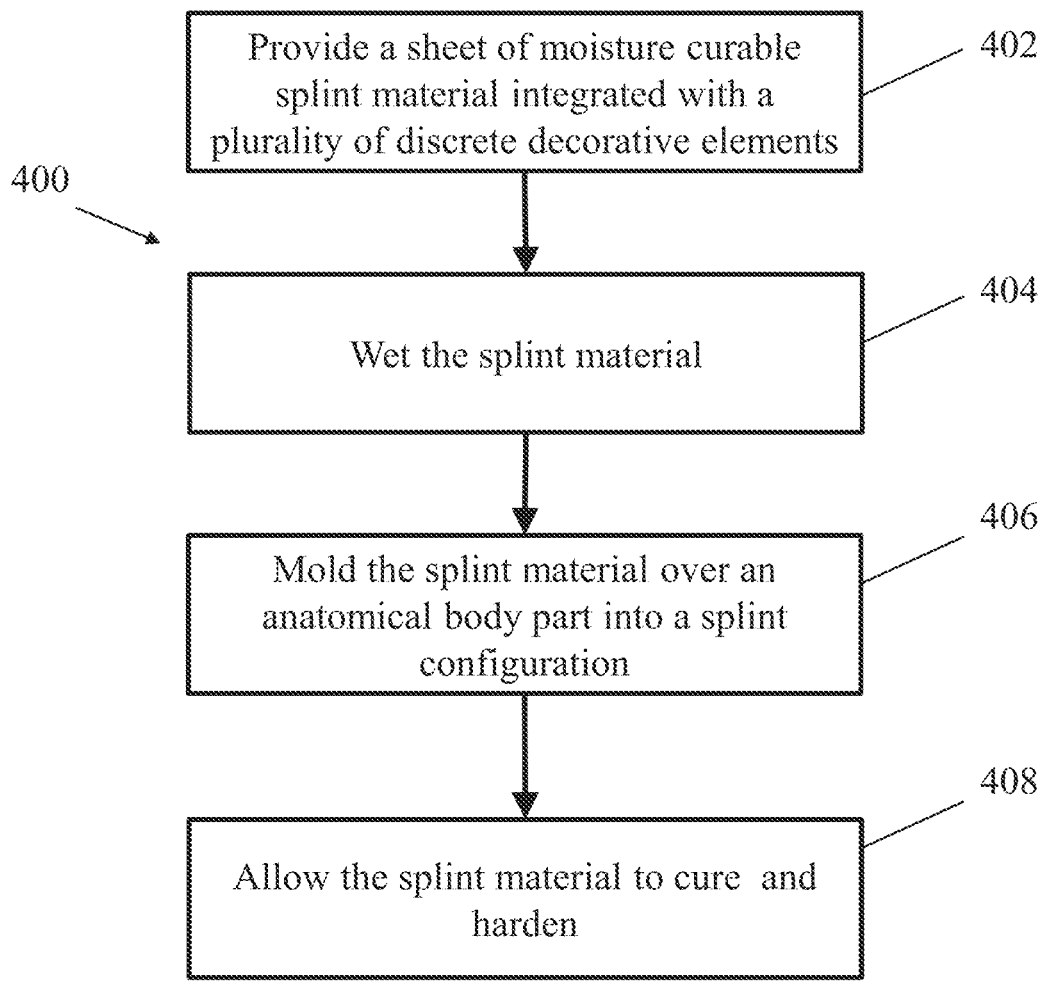
FIG. 4 is a flow chart of a method of applying a splint or cast to a patient according to one embodiment.

In one illustrative embodiment shown in FIG. 4, a method 400 of applying a splint to a patient may include providing a length of moisture-curable splint material (act 402) which has decorative elements that were previously integrated with the material. In some embodiments, a patient or doctor may select a length of splint material from among a number of color and or decorative options, where each length provides the same general immobilization and/or support functional properties.

The length of material is wetted (act 404), for example, by submerging the material into a container of water or by applying water to the material with a spray bottle or other applicator. In some embodiments, excess moisture may be removed from the material after wetting, for example, by wringing out the material. The material is wrapped around an anatomical body part (act 406) such that it forms a suitable splint configuration, and the splint material is allowed to cure (act 408) and harden such that the splint material retains the splint configuration. It should be understood that during the application of the splint, the decorative elements may remain integrated with the splint material such that the particular pattern and/or design of decorative elements is maintained. In some embodiments, the splint material may cure and harden over several minutes, and during curing, the splint material may remain pliable for a sufficient amount of time to permit shaping and applying the splint to the patient.

In some embodiments, the curing time and/or the amount of time the splint material remains pliable may be controlled during wetting of the splint material (act 404). For example, if a longer curing time is desired, excess moisture may not be removed from the splint material. Further, some moisture-curable splint materials may have a curing time which depends on the temperature of the water which is used to wet the splint material. For example, using colder water may allow for a longer curing time, while using warmer water may shorten the curing time.

In some embodiments, the moisture-curable splint material may undesirably adhere to a patient's skin. Therefore, in such embodiments, a separate underlayer such as a cotton sheet or other fabric sheet may be applied to the patient before applying the splint material to the body part. Such an underlayer may provide a protective barrier between the splint material and the body part while still allowing the splint material to provide suitable support. In some embodiments, the underlayer may be attached to the splint material.

The moisture-curable splint material may be self-bonding such that sections of wetted material may be pressed against other sections of wetted material. In this manner, the sections may join and remain joined when the material cures and hardens.

In some embodiments, the material may be molded into a splint shape without shaping the material directly on the patient. For example, the material may be wetted and then formed into a splint shape by pressing the material over a mold, or simply by molding the material with one's hands.

The molded splint may be cured (act 408) to a degree at which the splint material hardens. For purposes herein, curing refers to a chemical reaction taking place within the splint material between a resin, for example a polyurethane resin, and moisture such as water. During curing, the resin may polymerize to form a polymer structure which is substantially harder than the non-polymerized resin. For purposes herein, as relating to sheets of moisture-curable splint material, the term "harden" means bringing the material to a state where the material is resistant to a permanent shape change under typical handling forces.

Figure 5:
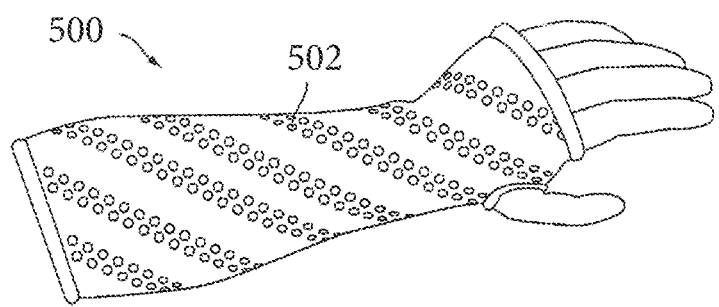
FIG. 5 shows splint material wrapped about a patient's wrist with the splint material including integrated decorative elements according to one embodiment.

FIG. 5 shows a decorated splint 500 formed by wrapping a splint material with integrated decorative elements 502 in a diagonal pattern around a patient's wrist. Dashed lines indicate edges of the splint material where the splint material overlaps adjacent splint material as a result of the wrapping process. While embodiments disclosed herein may be used to integrate the decorative elements with the splint material before the splint is molded on the patient, additional decorative elements may be added to the splint after the splint has been applied to the patient for customization of the design. For example, after the splint hardens, additional decorative elements may be adhered to the splint.

The various layers used for forming the splints disclosed herein may be provided in various colors, for example by including dyes within the moisture-curable material or flexible layer. In some embodiments, splint material may have color added after the splint material has been manufactured, for example by painting the assembled splint material.

Figure 6A:
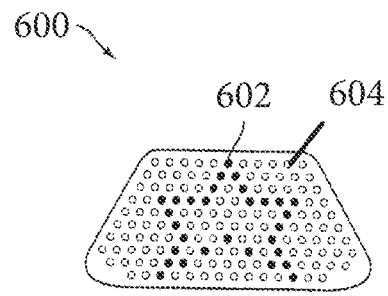
FIG. 6A is a top view of a sheet of splint or cast material including decorative elements according to one embodiment.
Figure 6B:
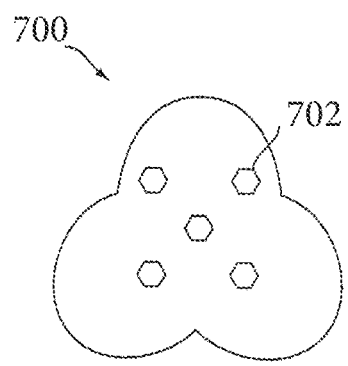
FIG. 6B is a top view of a sheet of splint or cast material including decorative elements according to another embodiment.

As indicated above, a moisture-curable, decorative splint may be provided as a sheet in various shapes. For example, a trapezoid-shaped sheet 600 is shown in FIG. 6a with beads 602 joined in a star design. The sheet 600 also includes a plurality of perforations 604, which may allow for breathability of the splint material, as described above. Of course any other desired type of decorative element may be used. FIG. 6b shows a sheet 700 which may be particularly suited for use as a nose splint and includes jewels 702 integrated with the sheet.

Having thus described several aspects of at least one embodiment, it is to be appreciated various alterations, modifications, and improvements will readily occur to those skilled in the art. Such alterations, modifications, and improvements are intended to be part of this disclosure, and are intended to be within the scope of the present disclosure. Accordingly, the foregoing description and drawings are by way of example only.

What is claimed is:

1. A decorative splint material comprising:
   a splint material that is moldable over an anatomical body part in a splint configuration and is configured to harden to retain the splint configuration; and
   a plurality of separate decorative elements integrated with the splint material, the decorative elements to be retained by the splint material when the splint material is being molded over an anatomical body part; wherein each of the plurality of decorative elements includes a decorative upper portion with an upper surface and a lateral portion that extends laterally beyond the decorative upper portion, the lateral portion being overlaid by a material to help secure the decorative element to the splint material, the upper surface being exposed and free of the material overlaying the lateral portion.

2. A decorative splint material as in claim 1, wherein the splint material includes one or more layers of fiberglass fabric impregnated with a moisture-curable polyurethane resin.

3. A decorative splint material as in claim 2, wherein the splint material includes one or more areas comprising a thermoplastic material.

4. A decorative splint material as in claim 1, wherein the splint material includes one or more areas comprising a thermoplastic material.

5. A decorative splint material as in claim 4, wherein the thermoplastic material holds the decorative elements in place.

6. A decorative splint material as in claim 1, wherein the decorative elements are attached to a mesh.

7. A decorative splint material as in claim 6, wherein the mesh comprises a mesh of plastic filaments.

8. A decorative splint material as in claim 1, wherein the lateral portion comprises a base of the decorative element.

9. A decorative splint material as in claim 1, wherein the decorative elements protrude beyond an outer surface of the splint material.

* * * * *